(12) United States Patent

Wang et al.

(10) Patent No.: US 8,748,594 B2
(45) Date of Patent: Jun. 10, 2014

(54) PROCESS FOR THE PREPARATION AND PURIFICATION OF TOPIRAMATE

(75) Inventors: Lung-Hu Wang, Kaohsiung (TW); Chun-Teng Huang, Jiali Township, Tainan County (TW)

(73) Assignee: Scinopharm Taiwan, Ltd., Tainan (TW)

( * ) Notice: Subject to any disclaimer, the term of this patent is extended or adjusted under 35 U.S.C. 154(b) by 119 days.

(21) Appl. No.: 13/512,355

(22) PCT Filed: Feb. 5, 2010

(86) PCT No.: PCT/US2010/023353
§ 371 (c)(1),
(2), (4) Date: May 29, 2012

(87) PCT Pub. No.: WO2011/096934
PCT Pub. Date: Aug. 11, 2011

(65) Prior Publication Data
US 2012/0232258 A1      Sep. 13, 2012

(51) Int. Cl.
*C07H 1/00*   (2006.01)
*C07H 3/00*   (2006.01)
*C08B 37/00*  (2006.01)

(52) U.S. Cl.
USPC .......................................................... 536/124

(58) Field of Classification Search
None
See application file for complete search history.

(56) References Cited

U.S. PATENT DOCUMENTS 4,513,006 A     4/1985   Maryanoff et al.

FOREIGN PATENT DOCUMENTS

| EP | 0533483 A2 | 3/1993 |
| WO | WO-2004/041836 A1 | 5/2004 |
| WO | WO-2004/089965 A2 | 10/2004 |

OTHER PUBLICATIONS

Oxford Dictionary of Chemistry definition for "one-pot synthesis," 2008.*

* cited by examiner

*Primary Examiner* — Layla Bland
(74) *Attorney, Agent, or Firm* — Enshan Hong; Kent H. Cheng; VLP Law Group LLP

(57) ABSTRACT

A process for the preparation of topiramate in an one pot reaction comprises the following steps: A) reacting 2,3:4,5-bis-O-{1-methylethylidene)-β-D-fructopyranose with sulfurylchloride in xylene in the presence of an organic or inorganic base to form 2,3:4,5-bis-O-(1-methylethylidene)-β-D-fructopyranose sulfuryl chloride, B) adding a second organic solvent to the mixture obtained in step A) C) reacting the mixture obtained in step B) with ammonia to form topiramate.

13 Claims, No Drawings

PROCESS FOR THE PREPARATION AND PURIFICATION OF TOPIRAMATE

RELATED APPLICATIONS

This is a U.S. national stage of application No. PCT/US10/23353, filed on Feb. 5, 2010.

BACKGROUND OF THE INVENTION

1. Field of the Invention

This invention relates to an efficient one-pot reaction process for the preparation of 2,3:4,5-bis-O-(1-methylethylidene)-β-D-fructopyranose sulfamate (topiramate) with the following chemical formula:

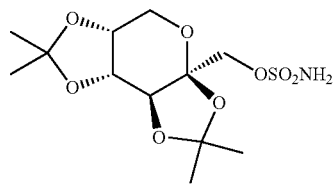

The invention also demonstrates a novel way for the purification of topiramate.

2. Description of the Related Art

Topiramate is a sulfamate substituted monosaccharide derivative which is useful in the treatment of epilepsy, obesity, bipolar disorder, neuropathic pain, migraine and smoking cessation. Topiramate acts as a carbonate dehydratase inhibitor, sodium channel blocker, AMPA antagonist, GABA agonist, and glutamate antagonist.

U.S. Pat. No. 4,513,006 discloses several processes for the preparation of topiramate. One of the described processes involves the reaction of protected fructopyranose with sulfuryl choride of the formula $SO_2Cl_2$ in the presence of a base in a dialkyl ether or methylene chloride solvent to produce the corresponding chlorosulfate:

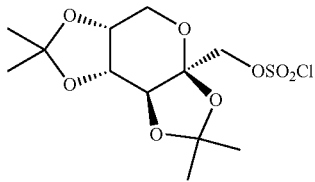

The chlorosulfate may then be reacted with ammonia in a methylene chloride or acetonitrile solvent to produce topiramate. This process produces relatively low yields of the desired end product.

The European patent application EP 0 533 483 A2 describes a process according to the above described reaction sequence giving rise to improved yields of the desired product. According to EP 0 533 483 A2, the reason for the high yields is to particularly select reaction solvents from toluene, t-butyl methyl ether or tetrahydrofuran (THF) for the chlorosulfonation step, and from THF, t-butyl methyl ether, toluene and lower alkanol for the amination step as well.

PCT application WO 2004/041836 A1 discloses a continuous process for the preparation of topiramate using the above-mentioned chlorosulfonation step and amination step. This continuous process involves carrying out the chlorosulfonation step in a solvent selected from a cyclic ether, a straight or branched chain dialkyl ether, and an aromatic hydrocarbon, or a mixture thereof, particularly glyme. The amination step is carried out in a second organic solvent comprising at least the solvent used in the chlorosulfonation step, particularly in glyme.

However, the yields of topiramate obtained by the processes described before are still not satisfactory, particularly as far as bulk production is concerned.

SUMMARY OF THE INVENTION

It is an object of the present invention to provide a process for the preparation of topiramate which produces high yields, particularly in bulk processes.

The present invention provides in an embodiment an improved process for the production of topiramate. This process comprises the above described steps of (i) conducting a chlorosulfonation of protected fructopyranose and (ii) subsequently carrying out an amination step in a one-pot reaction. The process of the present invention comprises:

A) reacting 2,3:4,5-bis-O-(1-methylethylidene)-β-D-fructopyrano se with sulfuryl chloride in xylene or a mixture of xylenes as a first organic solvent in the presence of an organic or inorganic base to form 2,3:4,5-bis-O-(1-methylethylidene)-3-D-fructopyrano se sulfuryl chloride (according to the present invention also called chlorosulfate), B) adding a second organic solvent to the mixture obtained in step A), C) reacting the mixture obtained in step B) with ammonia to form topiramate.

DETAILED DESCRIPTION OF THE PRESENTLY PREFERRED EMBODIMENTS

It was found that the use of xylene or mixtures of xylenes gives rise to improved yields compared to reactions using the solvents described in the prior art. Thus, improved yields are attributed to the fact that xylenes are almost insoluble in water and, therefore, the water content of xylenes—e.g. commercially available xylenes—is extremely low. According to the present invention, however, it was discovered that the presence of water during the amination step has a detrimental effect on the yield of the desired product. The chlorosulfate decomposes easily when being exposed to water and nucleophilic base (e.g. ammonia). Therefore, the presence of water will dramatically increase the decomposition of chlorosulfate, during conducting the subsequent amination step.

"Xylene" encompasses the ortho-, meta-, and para-isomers of dimethyl benzene. According to the present invention, either a pure isomer or a mixture of two or all three isomers is possible. In the following the term "xylene" is used for pure isomers as well as mixtures of isomers.

According to a further embodiment of the present invention, instead of xylene, also other solvents with low water content may be used as first organic solvent of the present invention. Appropriate solvents with low water content usually show a solubility in water which is less than 150 mg/l. Particularly, aromatic solvents have to be mentioned, more particularly aromatic solvents which are pure hydrocarbons, for example solvents like ethylbenzene and solvents having a lower solubility in water compared to ethylbenzene.

Before the amination step is carried out, usually a second organic solvent is added to the mixture obtained after the chlorosulfonation step A). The second organic solvent is selected from solvents that could provide good solubility of ammonia, do not react with the chlorosulfate, and usually from solvents that have a lower boiling point compared to the first organic solvent. Preferably, the second organic solvent is selected from aprotic ethers, such as diethyl ether and tetrahydrofuran.

Step C) of the present invention can be carried out by any possible method. For example, the different methods described in EP 533 483 A2 are applicable.

The organic or inorganic base used in the present invention may be any appropriate base, for example a carbonate containing base or a nitrogen containing organic base. Preferably, the organic or inorganic base is soluble in the first organic solvent or at least partially soluble. Without confining the generality of the present invention, the base may be selected from alkali carbonates like sodium carbonate, potassium carbonate and sodium hydrogen carbonate as inorganic bases and/or from tertiary amine, nitrogen containing heterocycles such as pyridine, pyridine derivatives, TEA, DIPEA, and the like and mixtures of aforesaid organic and/or inorganic bases. Usually, organic tertiary amine bases or pyridine are used as base.

According to a further embodiment, between step A) and step B), the following steps D), E) and F) are carried out:
  In step D), the mixture obtained in step A) (i.e. the chlorosulfate) is washed at least once with a first aqueous washing agent.
  In step E), the organic layer or the organic layers obtained in step D) are collected; said collected organic layers are subsequently dried with a drying agent in step F).

Again, the additional steps of this embodiment are based on the finding that the reaction product of the chlorosulfonation step is sensitive to water and nucleophilic base (e.g. ammonia used in the subsequent amination step), therefore, traces of water contained in the first organic solvent should be avoided. Nevertheless, for reasons of purification, washing the reaction mixture obtained in the chlorosulfonation step with an aqueous solvent is expedient. In order to remove traces of water from the first organic solvent, step F) is carried out, wherein the first organic solvent containing the mixture obtained in step E) is dried.

The first aqueous washing agent may be selected from water, an aqueous solution of a salt, an aqueous solution of an acid, and mixtures thereof. An example for an aqueous solution of a salt is a solution of sodium chloride; examples for aqueous solutions of an acid are solutions of hydrochloric acid or of citric acid or other organic acids.

As drying agent, for example, water absorbing salts or molecular sieves can be used. The water absorbing salt may, for example, be selected from the group consisting of magnesium sulfate, sodium sulfate, calcium chloride, and mixtures thereof. In theory, also chemical reagents reacting with water may be used when a reaction of these reagents with the chlorosulfate does not take place.

According to a further embodiment, step A) of the present invention is carried out in three partial steps A1), A2) and A3):
  In step A1),
    2,3:4,5-bis-O-(1-methylethylidene)-β-D-fructopyrano se is mixed with the first organic solvent and in step A2), the mixture obtained in step A1) is distilled in order to remove water. Subsequently, in step A3), the distilled mixture is reacted with sulfuryl chloride in the presence of the organic or inorganic base.

Again, the intention of this steps A1) to A3) is to further remove any trace of water, particularly from the reaction mixture of the chlorosulfonation step. Therefore, a mixture of the first organic solvent and the starting material, i.e. the protected fructopyranose, is distilled thereby removing traces of water being present in the starting material and/or the used first organic solvent. For example, for carrying out the distillation of step A2), a distilling trap could be used, wherein water is collected (for example using the principle of a Dean-Stark apparatus). The solvents usually used as first organic solvents exhibit boiling points being much higher than the boiling point of water. Therefore, water can be evaporated relatively easily.

As already mentioned, the amination step, i.e. step C), may be carried out as known from the state of the art. Preferably, as second organic solvent tetrahydrofuran is used. Furthermore, process step C) is preferably conducted at a temperature below 0° C. After the chlorosulfonation step is completed (optionally after having carried out the above mentioned washing steps), the first organic solvent is not needed to be removed. Therefore, the distillation step (after having the chlorosulfonation step) carried out in the prior art, such as EP 0 533 483 A2 and WO 2004/041836, can be skipped in the present invention. The distillation step may cause more decomposition of the unstable intermediate, chlorosulfate.

In an embodiment of the present invention, after step C) (i.e. after having carried out the amination step), the following step G) is carried out:
  The reaction mixture obtained in step C), containing the first organic solvent and the second organic solvent, is distilled in order to remove at least a part of the second organic solvent.

According to this embodiment, the second organic solvent has a lower boiling point compared to the boiling point of the first organic solvent. Usually, the boiling point of the second organic solvent is chosen so that upon distillation an easy separation of the second organic solvent is possible without substantially reducing the amount of the first organic solvent. For example, the second organic solvent may have a boiling point below 80° C., for example below 66° C. like THF.

If the first organic solvent is chosen to be xylene or also a solvent like ethylbenzene, reaction step G) may be carried out quite easily; the mixture obtained after distillation will usually contain the first organic solvent almost as the only solvent being present. In contrast, the solvents used according to the prior art do not show big differences of boiling points and therefore are not separable that easily. According to the present invention, the difference of boiling points of the first and the second organic solvent may be more than 50° C. or even 70° C. or more.

A further advantage of using a first and a second solvent with the described differences in boiling points is the possibility to remove almost all of the second organic solvent without removing all of the first organic solvent simultaneously, which would result in an oily product (as described in the prior art). In the present invention, topiramate usually is within the first organic solvent before being precipitated, which can reduce the decomposition caused by removing all of the solvent to obtain the crude reaction product in oil form. Therefore, the solvent system of the present invention gives rise for a further improved yield.

According to a further embodiment, the reaction mixture obtained after step C) is purified by carrying out steps H) and I):
  In step H), the reaction mixture obtained in step C) is washed at least once with a second aqueous washing agent selected from water and an aqueous solution; in step I), the organic layers of step H) are collected.

The second aqueous washing agent may be selected from water, and aqueous solutions of a salt.

In embodiments where step G) as well as steps H) and I) are carried out, usually the order of the steps is: C) /H) /I) /G).

According to a further embodiment, after step C) (i.e. after having carried out the amination step), the following steps J) and K) are carried out:

In step J), a third solvent is added to the mixture obtained in step C) and in step K) a precipitation of topiramate from the mixture obtained in step J) is caused.

Often steps J) and K) take place simultaneously. However, a separate step k) may, for example, take place by cooling down the mixture obtained in step J) causing precipitation of the desired product or causing additional precipitation of the desired product. However, precipitation may not only be caused by cooling down the obtained mixture; also other techniques, for example the use of seed crystals, are alternatively of additionally possible.

The third solvent added in step J) is usually selected from solvents wherein topiramate is compared to the first organic solvent less soluble. Usually, alkanes, particularly n-alkanes, may be used as third solvent, for example n-pentane, n-heptane and/or n-hexane. In one embodiment of the present invention, n-heptane is added to facilitate the precipitation of topiramate while xylene is still present in the reaction mixture. The solubility of topiramate in xylene is quite low, which can facilitate to reduce the loss of topiramate in the mother liquid.

The present invention is further directed to a process for purification of topiramate.

According to the present invention, a process for the purification of topiramate may be carried out by recrystallising crude topiramate from a mixture containing isopropanol and n-heptane or a mixture consisting of said solvents.

According to the present invention, it was discovered that by using this solvent system topiramate with particularly high purity may be obtained in high yields. The process of purification may, even in bulk reactions, be carried out operationally simple.

Purification according to the present invention refers to methods wherein the crude product is dissolved, optionally at elevated temperature, and the dissolved product is precipitated by adding an appropriate solvent (i.e. an "anti-solvent") and/or by cooling the solution and the like. Before the precipitation starts, also procedures like filtration of the obtained solution may be carried out.

The process of the present invention is described by the following examples, which are illustrative only and should not be construed so as to limit the scope of the invention in any manner.

EXAMPLE 1

Preparation of Topiramate (Chlorosulfonation)

A suitable reactor was charged with xylene (about 3 kg) and sulfuryl chloride (about 0.6 kg). The sulfuryl chloride solution was cooled to −20 to −5° C. A solution of 2,3:4,5-bis-O-(1-methylethylidene)-3-D-fructopyranose (about 1 kg) in xylene (about 4 kg) was charged to another suitable vessel. The reaction mixture in the vessel was distilled under vacuum to remove about 1 part (1 L) of solvent. After distillation, pyridine (about 0.4 kg) was added to the reaction mixture in the vessel. Then the mixture in the vessel was slowly added to the reactor, while maintaining the temperature at −20 to −5° C. The reaction mixture was stirred at a temperature below 10° C. until the chlorosulfonation was completed.

The chlorosulfonated mixture was transferred to a reactor containing pre-cool water (about 4 kg). The organic layer was separated and washed with citric acid solution (about 3 kg) while maintaining the temperature below 10° C. The organic layer was collected and washed with sodium acetate solution (about 5 kg) while maintaining the temperature below 10° C. The aqueous phase was removed and magnesium sulfate anhydrous (about 0.02 kg) was added to the organic phase. The mixture was stirred, and then filtered to get 2,3:4,5-bis-O-(1-methylethylidene)-β-D-fructopyranose sulfuryl chloride (chlorosulfate) in xylene.

(Amination)

Tetrahydrofuran (about 7.5 kg) was added to the solution containing chlorosulfate and the resultant solution was cooled to below 0° C. Ammonia gas and nitrogen gas were charged into the reaction mixture until the amination reaction was completed, while maintaining the temperature below 0° C. Water (about 2 kg) was added and the mixture stirred at a temperature below 10° C. The organic layer was collected and washed again with water (about 2.0 kg) at a temperature below 10° C. The organic phase was filtered and then distilled under vacuum until the residual mixture was approximately free of tetrahydrofuran. N-heptane (about 2.7 kg) was added. The resultant slurry was cooled to below 10° C., filtered and washed with n-heptane to give the crude topiramate (about 0.91 kg to 1.235 kg on a dry basis).

Expected overall yield:80-95%

(Recrystallization)

The crude topiramate (about 1 kg) and isopropanol (about 1 kg) were charged to a suitable reactor. The resulting mixture was heated until the topiramate was dissolved. The solution was filtered. N-heptane (about 2 kg) was added slowly at 60 to 75° C. The solution was cooled and followed by seeded with topiramate (about 0.002 kg). The mixture was agitated and then cooled to below 10° C. slowly. The resulting solution was agitated and then transferred to a suitable vessel while controlling the internal temperature below 10° C. The slurry was filtered. The cake was dried under vacuum to give topiramate (about 0.80 kg to 0.95 kg).

EXAMPLE 2

The Removal of Water

In the prior art, such as EP 0 533 483 A2 and WO 2004/041836, the distillation step was carried out to remove solvent to give the chlorosulfate in oil form. On the contrary, in the present invention, no distillation is conducted to the reaction mixture containing the chlorosulfate. The drying agent, magnesium sulfate, may be used to replace the distillation step carried out in the prior art. Therefore, in the present invention, the removal of water can be carried out in a less destructive way.

In order to demonstrate that the removal of water is critical in the process of preparing topiramate, the following (comparative) experiments were carried out.

Experiment 2.1 was carried out as the chlorosulfonation and amination steps described in example 1 except for the following two points.

(1) The charged 2,3:4,5-bis-O-(1-methylethylidene)-β-D-fructopyranose was about 25 g. The charged amounts for other reagents and solvent were reduced proportionally.

(2) Magnesium sulfate was not added into the resultant solution containing the chlorosulfate.

Experiment 2.1 represents the example without water-removal procedure.

Experiment 2.2 was carried out as the chlorosulfonation and amination steps described in example 1 except for the following three points.

(1) The charged 2,3:4,5-bis-O-(1-methylethylidene)-β-D-fructopyranose was about 25 g. The charged amounts for other reagents and solvent were reduced proportionally.

(2) Magnesium sulfate was not added into the resultant solution containing the chlorosulfate.

(3) Distillation step was carried out after conducting the extraction steps (washing with water, citric acid solution and sodium acetate solution). The distillation was carried out at less than 45° C. and a pressure less than 5 Torr, similar as disclosed in the prior art.

The following table shows the results with respect to the purity and yield of crude topiramate (before recrystallisation from isopropanol/n-heptane) compared to the results obtained in example 1.

TABLE 1

|  | Experiment 2.1 Without water-removal | Experiment 2.2 Distillation | Example 1 according to the invention |
|---|---|---|---|
| Purity of the crude topiramate | 31% (HPLC) | 99.3% (HPLC) | 99.4% (HPLC) |
| Yield of the Crude topiramate | 10% | 74% | 83% |

Table 1 shows if water-removal procedure is not carried out, the purity and yield of topiramate will be significantly reduced.

EXAMPLE 3

Solvent Effect

As comparing to the prior art, the first organic solvent, xylene, is not removed from the reaction mixture in the present invention. The remained xylene offers a protective effect to the chlorosulfate and topiramate contained in it. However, the yield will be decreased because more topiramate is dissolved in the remained organic solvent.

In order to demonstrate that the solubility of topiramate in the first organic solvent is critical in the present invention, the following experiments were carried out.

Experiment 3.1 was carried out as the chlorosulfonation and amination steps described in example 1 except for the charged amounts of the solvents and reagents. In Experiment 3.1, the charged 2,3:4,5-bis-O-(1-methylethylidene)-β-D-fructopyranose was about 50 g. The charged amounts for other reagents and solvent were reduced proportionally.

Experiment 3.2 was carried out as the chlorosulfonation and amination steps described in example 1 except for the charged amounts of the solvents and reagents (the same as that in Experiment 3.1), and using toluene as the first organic solvent instead of xylene.

The following amounts were detected:

(1) Chlorosulfate decomposing to the starting material, 2,3:4,5-bis-O-(1-methylethylidene)-β-D-fructopyranos e, during the amination step (2) loss during precipitation of topiramate by adding n-Heptane Table 2 shows the loss of yield during said steps. Additionally, the purity and yield of the obtained topiramate (before recrystallisation from isopropanol/n-heptane) are given in Table 2.

TABLE 2

| Procedure/step | Experiment 3.1 Using xylene as the first solvent | Experiment 3.2 Using toluene as the first solvent |
|---|---|---|
| Decomposition of chlorosulfate during amination: step C) | 10.3% | 15.0% |
| Loss of product during precipitation with n-Heptane: step J)/K) | 1.2% | 3.6% |
| Yield of the crude topiramate | 81.0% | 68.7% |
| Purity of the crude topiramate | 99.2% (HPLC) | 98.7% (HPLC) |

The results of Table 2 show that a particularly high loss of yield can be detected during the amination step due to decomposition of the chlorosulfate intermediate (usually decomposing to starting material). The water solubility of toluene is about 540 to 580 mg/L, and that of xylene is about 198 mg/L. Therefore, the moisture absorbility of toluene should be much higher than that of xylene. This fact may lead to the higher loss in yield when using toluene as the first solvent, as during the amination step, toluene may expose to moisture and bring more water into the reaction mixture.

It was further observed that the yield during the precipitation step can be improved when using xylene instead of toluene in the present invention. This is attributed to the fact that topiramate is less soluble in xylene compared to toluene. The solubility of topiramate in xylene was detected to be 0.0025 mg per mg xylene whereas the solubility of topiramate in toluene is 0.008 mg per mg solvent. Therefore, when using xylene as the first solvent in the present invention, the loss of topiramate in the mother liquid can be reduced.

The present examples are to be considered as illustrative and not restrictive, and the invention was not limited to the details given herein but may be modified within the scope and equivalents of the appended claims.

The invention claimed is:

1. A process for the preparation of topiramate or a pharmaceutically acceptable salt thereof, wherein the process comprises the following steps:
Aa) reacting 2,3:4,5-bis-O-(1-methylethylidene)-β-D-fructopyranose with sulfurylchloride in xylene or a mixture of xylenes as a first organic solvent in the presence of an organic or inorganic base to form 2,3:4,5-bis-O-(1-methylethylidene)-β-D-fructopyranose sulfuryl chloride,
Ab) washing the mixture obtained in step Aa) at least once with a first aqueous washing agent;
Ac) collecting the organic layer of the mixture obtained in step Ab);
Ad) drying the organic layer obtained in step Ac with a drying agent;
B) adding a second organic solvent to the dried organic layer obtained in step Ad), wherein the second organic solvent has a lower boiling point compared to the boiling point of xylene, and
C) reacting the mixture obtained in step B) with ammonia to form topiramate.

2. A process for preparation of topiramate or a pharmaceutically acceptable salt thereof, wherein the process comprises the following steps:
1) mixing 2,3:4,5-bis-O-(1-methylethylidene)-β-D-fructopyranose with a first organic solvent, which is a xylene or a mixture of xylenes, 2) distilling the mixture obtained in step 1) to remove water;
3) reacting the mixture of step 2) with sulfurylchloride in the presence of an organic or inorganic base to form 2,3:4,5-bis-O-(1-methylethylidene)-β-D-fructopyranose sulfuryl chloride;
4) adding a second organic solvent to the mixture obtained in step 3), wherein the second organic solvent has a lower boiling point compared to the boiling point of xylene, and
5) reacting the mixture obtained in step 4) with ammonia to form topiramate.

3. The process according to claim 1, wherein step Ab) is conducted at not more than 10° C.

4. The process according to claim 1, wherein the second organic solvent is tetrahydrofuran.

5. The process according to claim 1, wherein step C) is conducted at a temperature below 0° C.

6. The process according to claim 1, wherein after step C) the following step is carried out:
G) distilling the mixture obtained in step C), containing the first organic solvent and the second organic solvent, to remove the second organic solvent at least partially.

7. The process according to claim 1, wherein after step C) the following step is carried out:
H) washing the mixture obtained in step C) at least once with a second aqueous washing agent, selected from water and an aqueous solution, and
I) collecting the organic layer of the mixture obtained in step H).

8. The process according to claim 1, wherein after step C) the following steps are carried out:
J) adding a third solvent into the mixture obtained in step C), and
K) causing precipitation of topiramate from the mixture obtained in step J).

9. The process according to claim 8, wherein the third solvent is an alkane.

10. The process according to claim 1, wherein the organic or inorganic base is a heterocyclic compound and/or an amine.

11. The process according to claim 1, wherein the drying agent is a water adsorbing salt or a molecular sieve.

12. The process according to claim 11, wherein the water adsorbing salt is selected from the group consisting of $MgSO_4$, $Na_2SO_4$, $CaCl_2$ and mixtures of aforesaid compounds.

13. The process of claim 1 wherein the topiramate obtained in step C) is further purified by recrystallisation from a mixture containing or consisting of isopropanol and n-heptane.

* * * * *